United States Patent
Fan et al.

(10) Patent No.: US 9,554,770 B2
(45) Date of Patent: Jan. 31, 2017

(54) HIGH PULSE REPETITION FREQUENCY FOR DETECTION OF TISSUE MECHANICAL PROPERTY WITH ULTRASOUND

(75) Inventors: Liexiang Fan, Sammamish, WA (US); Richard Chiao, Cupertino, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1215 days.

(21) Appl. No.: 12/240,044

(22) Filed: Sep. 29, 2008

(65) Prior Publication Data

US 2010/0286516 A1 Nov. 11, 2010

(51) Int. Cl.
*A61B 8/08* (2006.01)
*G01S 7/52* (2006.01)
*G01S 15/89* (2006.01)

(52) U.S. Cl.
CPC .............. *A61B 8/08* (2013.01); *A61B 8/485* (2013.01); *G01S 7/52036* (2013.01); *G01S 15/8959* (2013.01)

(58) Field of Classification Search
USPC ............ 600/437–440, 443; 73/570, 573–575
See application file for complete search history.

(56) References Cited

U.S. PATENT DOCUMENTS

| | | | |
|---|---|---|---|
| 4,053,884 A | 10/1977 | Cantrell et al. | |
| 4,746,922 A | 5/1988 | Prenat | |
| 5,107,837 A | 4/1992 | Ophir et al. | |
| 5,178,147 A | 1/1993 | Ophir et al. | |
| 5,293,870 A | 3/1994 | Ophir et al. | |
| 5,606,971 A * | 3/1997 | Sarvazyan | 600/438 |
| 5,726,657 A | 3/1998 | Pergande et al. | |
| 5,964,707 A | 10/1999 | Fenster et al. | |
| 6,027,448 A * | 2/2000 | Hossack et al. | 600/447 |
| 6,232,912 B1 | 5/2001 | Nagel | |
| 6,508,768 B1 | 1/2003 | Hall et al. | |
| 6,547,733 B2 * | 4/2003 | Hwang et al. | 600/437 |
| 6,561,981 B2 * | 5/2003 | Bonnefous | 600/443 |
| 6,989,782 B2 | 1/2006 | Walker et al. | |
| 7,175,599 B2 * | 2/2007 | Hynynen et al. | 600/443 |
| 2004/0081340 A1 * | 4/2004 | Hashimoto | 382/128 |
| 2004/0167403 A1 * | 8/2004 | Nightingale et al. | 600/437 |
| 2007/0073145 A1 | 3/2007 | Fan et al. | |
| 2008/0021319 A1 * | 1/2008 | Hamilton | 600/437 |
| 2008/0097207 A1 | 4/2008 | Cai | |

OTHER PUBLICATIONS

U.S. Appl. No. 11/824,388, filed Jun. 28, 2007.
U.S. Appl. No. 12/027,957, filed Feb. 7, 2008.
(Continued)

*Primary Examiner* — Joseph M Santos Rodriguez

(57) ABSTRACT

Detection of tissue response is provided with a high pulse repetition frequency. A sequence of separable signals is transmitted in one event. For example, pulses at different frequencies are transmitted as separate waveforms, but in rapid succession. As another example, coded transmit pulses are used. After transmission of the pulses, signals are received. Based on the different frequencies or coding, tissue response is measured at different times based on the receive event. Instead of one measure, a plurality of measures are provided for a given transmit and receive event pair, increasing the effective pulse repetition frequency for shear or elasticity imaging.

7 Claims, 4 Drawing Sheets

(56) References Cited

OTHER PUBLICATIONS

U.S. Appl. No. 12/038,683, filed Feb. 27, 2008.
U.S. Appl. No. 12/174,011, filed Jul. 16, 2008.
Pinton, et al., "Rapid Tracking of Small Displacements Using Ultrasound", 2005 IEEE Ultrasonics Symposium, pp. 2062-2065.
Sarvazyan, et al., "Shear Wave Elasticity Imaging: A New Ultrasonic Technology of Medical Diagnostics", Ultrasound in Med. & Biol., vol. 24, No. 9, pp. 1419-1435; 1998.
Nightingale, et al., "Shear Wave Velocity Estimation Using Acoustic Radiation Force Impulsive Excitation in Liver in Vivo", 2006 IEEE Ultrasonics Symposium, pp. 1156-1160.

\* cited by examiner

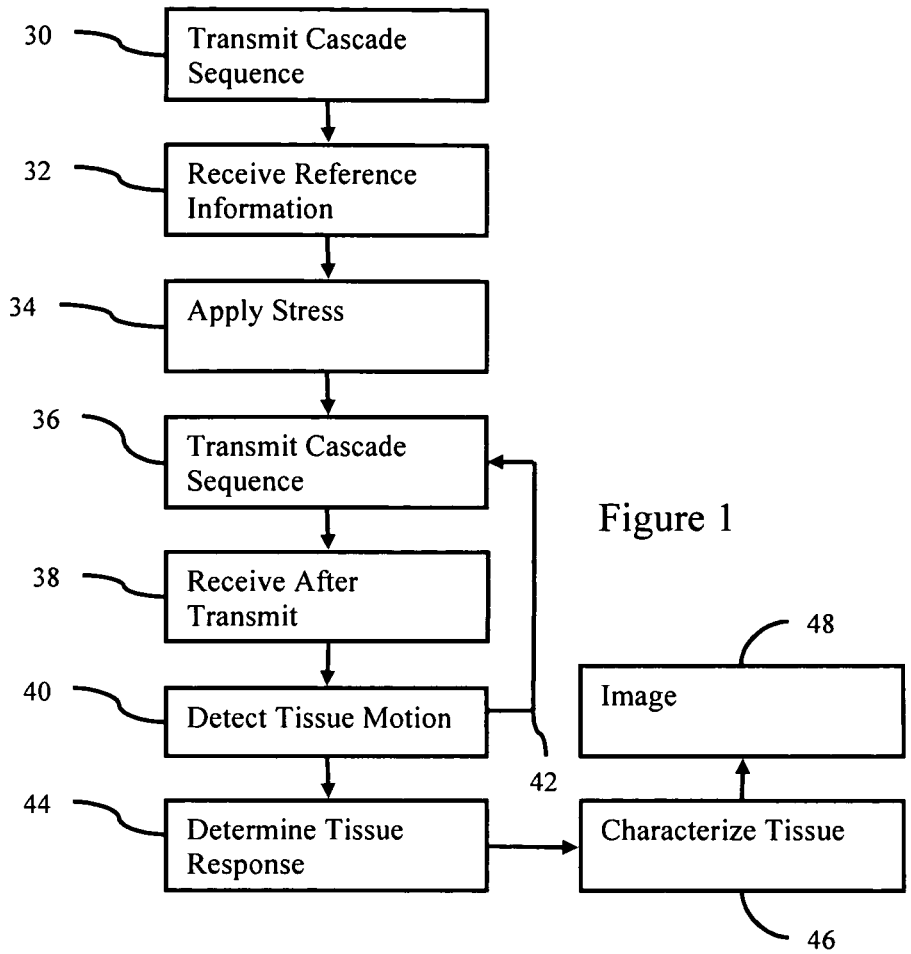
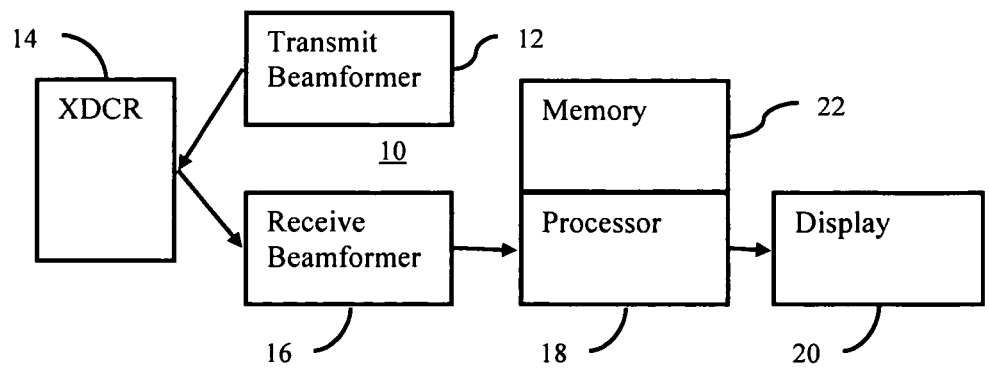

HIGH PULSE REPETITION FREQUENCY FOR DETECTION OF TISSUE MECHANICAL PROPERTY WITH ULTRASOUND

BACKGROUND

The present embodiments relate to detection with ultrasound of tissue properties. Ultrasound may be used to detect a shear wave or displacement in tissue.

Shear is a viscoelastic property of tissue. The shear wave velocity of tissue may indicate useful information about the health of the tissue. Shear wave images may be generated. A characteristic of the shear wave in the tissue is determined for different spatial locations. An image of the characteristic as a function of space is generated. However, a large number of transmissions and receptions are used to estimate shear wave information in a large region, resulting in a slow frame rate.

Another tissue property or component of viscoelasticity is elasticity. Ultrasound imaging may operate in an elasticity imaging mode. U.S. Pat. Nos. 5,107,837; 5,293,870; 5,178,147; and 6,508,768 describe methods to generate elasticity images using the relative tissue displacement between adjacent frames. The tissue strain is determined in response to a stress applied to tissue. The stress is applied externally, such as by manual pressure or by acoustic pressure. Strain or strain rate are detected for generating an elasticity image. Altered stiffness regions may be identified. However, strain is relative or qualitative. For example, different amounts of applied stress result in different amounts of strain. The amount of applied stress may be unknown or difficult to determine accurately.

BRIEF SUMMARY

By way of introduction, the preferred embodiments described below include methods, instructions, and systems for detection with a high pulse repetition frequency of tissue response. A sequence of separable signals is transmitted in one event. For example, pulses at different frequencies are transmitted as separate waveforms, but in rapid succession. As another example, coded transmit pulses are used. After transmission of the pulses, signals are received. Based on the different frequencies or coding, tissue response is measured at different times based on the receive event. Instead of one measure, a plurality of measures are provided for a given transmit and receive event pair, increasing the effective pulse repetition frequency for shear or elasticity imaging.

In a first aspect, a method is provided for detection with high pulse repetition frequency of tissue response. In a first transmit event, a plurality of ultrasound signals are transmitted to tissue responding to stress. The signals are mutually orthogonal. In a first receive event, ultrasound echoes responsive to the mutually orthogonal signals are received. Tissue motion is detected at a plurality of times corresponding to the plurality of signals, respectively, as a function of the received echoes from the first receive event. The tissue response is determined as a function of the tissue motion.

In a second aspect, a computer readable storage medium has stored therein data representing instructions executable by a programmed processor for detection with high pulse repetition frequency of tissue response. The storage medium includes instructions for transmitting a sequence of ultrasound pulses having different frequencies, after the transmitting of the sequence, receiving signals at the different frequencies, detecting tissue motion as a function of the signals at the different frequencies, and deriving the tissue response from the tissue motion.

In a third aspect, a system is provided for detection with high pulse repetition frequency of tissue response. A transmit beamformer is operable to transmit a cascade of pulses with mutually orthogonal codes. A receive beamformer is operable to filter with matching codes such that separate signals are generated. A processor is operable to detect tissue motion as a function of the separate signals. A display is operable to output tissue response as a function of the tissue motion.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a flow chart diagram of one embodiment of a method for detection with high pulse repetition frequency of tissue response;

FIG. 4 is a block diagram of one embodiment of a system for detection with high pulse repetition frequency of tissue response.

DETAILED DESCRIPTION OF THE DRAWINGS AND PRESENTLY PREFERRED EMBODIMENTS

Figure 2:
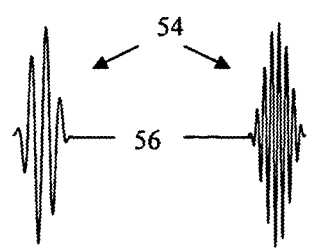
FIG. 2 is an example illustration of a sequence of pulses for transmission.

Acoustic radiation force impulse (ARFI) applied to a focused area induces a shear wave. In response, tissue's displacement increases and then recovers, resulting in a temporal displacement profile. The peak and its location of the displacement profile may be used to characterize a mechanical property of the tissue. Information relevant to clinics or research can be derived from monitoring the tissue's transient response with respect to pressure variation. Examples are the peak and the peak's location detection of ARFI induced shear wave propagation, and dynamic characteristics of contrast agents during high pulse excitation.

To improve the detection accuracy of peak location, velocity, or other tissue response, additional samples of displacement in time are measured. Repeatedly transmitting to and receiving signals from the same target area is used in estimating the displacement. Pulse repetition frequency (PRF) is the sampling rate of the temporal displacement profile and directly affects the accuracy of the peak location detection. The speed of sound in tissue limits the frequency of transmit and receive event pairs where a same element is used for transmit and receive. After a transmit event, the transmissions cease until the echoes have been received from the depths of interest. PRF in conventional ultrasound pulsing method is limited by the speed of sound and is not able to fulfill the task when the depth increases.

High sampling rate improves the accuracy. The PRF may be increased by transmitting N cascade transmit pulses with different center frequencies per transmit interval or event. The receive signals are demodulated with corresponding frequencies to generate N pairs of in-phase and quad-phase signals. The time interval between each pulse in the cascade transmit may be as short as system hardware loading and switch time limits. One receive event is used to form N samples. After M sets of N cascade pulses are transmitted and received, a total of MN displacement data points are estimated with respect to a reference. The temporal displacement profile is then reconstructed from these (M−1)N estimated displacements.

Other mutually orthogonal codes may be used. For example, a coded transmit waveform is used. The received signal is demodulated with a corresponding matched filter with corresponding codes to separate signals.

This method may be used to image tissue within the full field of view since high PRF is provided without requiring separate transmit and receive elements. High frame rate images may be generated.

FIG. 1 shows a method for detection with high pulse repetition frequency of tissue response. The method is implemented by the system of FIG. 4 or a different system. Additional, different, or fewer acts may be provided. For example, act 36 or acts 36, 38, and 40 are performed alone or in any combination. The acts are performed in the order described or shown, but may be performed in other orders.

In act 30, a sequence of pulses is transmitted to tissue prior to application of a stress. The transmission occurs before application of the stress and measurement of the tissue response to the stress. Since the tissue response to the stress may be measured before, after or both relative to the peak stress, the transmission for reference tissue position is performed prior to application of the stress. Where the stress is ongoing, the transmission may occur at a point relative to a cycle of stress.

The sequence is the same as provided in act 36, such as a being a sequence with mutually orthogonal pulses. Mutually orthogonal pulses may be separated into distinct signals. One set of N pulses is transmitted before ARFI is applied and is used to acquire reference data for displacement estimation. In other embodiments, separate transmit and receive events are performed for each component of the mutually orthogonal sequence of pulses used in act 36. Alternatively, transmissions at one frequency or without coding are used for obtaining the reference tissue information.

In act 32, reference information is received. Electrical signals generated by the transducer in response to echoes from the transmission are received. The signals are separated, such as by filtering, demodulation and filtering, or matched filtering. For example, in-phase and quadrature pairs of samples for each separable signal are generated. The separated signals are used to detect reference tissue information. Any type of detection may be used, such as a B-mode detection of the intensity. The detected information is responsive to the transmitting prior to application of the stress. Tissue may be detected separately for different frequencies. Alternatively, tissue is detected based on an average of different frequencies or based on one frequency.

In act 34, stress is applied to the tissue. For example, acoustic radiation force focused at the region of interest or a point is transmitted. When an acoustic radiation force impulse (ARFI) is applied to a focused area, a shear wave is induced and propagates away from this focused area. The shear wave stresses the tissue. The tissue responds to the stress by moving. Relative to an original location, tissue is displaced. This displacement increases and then recovers to zero, resulting in a temporal displacement profile.

Other sources of stress may be used, such as manually or internally generated stress. For example, a user applies pressure axially with a transducer. The stress may be added or released. The applied stress may be an impulse, cyclical, repeating, or a non-impulse stress. For example, the pressure applied due to breathing or the heart is cyclical. The stress is applied repetitively, or differently as a function of time. The applied stress may be represented by an impulse. A substantially single pressure wave is generated. The impulse may be generated by a cyclical pulsed waveform of any number of cycles (e.g., tens or hundreds of cycles). For example, acoustic radiation force is transmitted as an impulse for applying stress to tissue. The impulse wavefront propagates to the region of interest.

Acts 36 and 38 occur while the tissue is being subjected to and/or recovers from the stress. For example, transmission and reception occur after application or change in the stress and before the tissue reaches a relaxed state. The detection of motion in act 40 occurs in real-time with the reception of act 38, so occurs while the tissue is subjected to the stress. Alternatively, the detection of act 40 is performed from stored signals after the tissue reaches the relaxed state.

The response of tissue along transmit or receive beams is detected. Doppler or B-mode scanning may be used. Ultrasound imaging is performed before, during and/or after the stress is applied. Ultrasound data is received in response to transmissions of ultrasound. The transmissions and receptions are performed for a single spatial location (e.g., the focal point of the applied stress), along a line, over an area, or over a volume. A sequence of transmissions and receptions are provided for each spatial location.

In act 36, a plurality of ultrasound signals are transmitted to the tissue responding to the stress. The plurality of signals are transmitted in one transmit event. The transmit event is a contiguous interval where transmissions occur without reception of echoes responsive to the transmission. The contiguous interval of the transmit event may include one or more periods of no transmission. During the phase of transmitting, there is no receiving. Multiple transmit events may be provided where at least one of the transmit events includes the plurality of signals.

The signals of the sequence for a given transmit event are mutually orthogonal. The signals may be separated in time and/or space. Mutually orthogonal signals include pulses with different frequencies separated in time or some coded sequences. Coded waveforms include a waveform modulated by a code. The coding is mutually orthogonal, such as Golay codes.

By transmitting mutually orthogonal pulses, the pulse repetition frequency (PRF) may be increased. The PRF is the sampling rate of the temporal displacement profile and affects the accuracy of the peak location detection. High PRF with spatial determination is desired when shear wave velocity is high.

In one embodiment, the signals are transmitted as pulses having different frequencies. The multiple imaging pulses of the sequence have different center frequencies. The pulses may overlap in time. Alternatively, the pulses with different frequencies have no overlap and/or are separated by a period of no transmission. The period is short, such as just long enough for the transmitter to switch to a different frequency. Longer periods may be provided. Longer periods may result in no reception from an increased depth.

FIG. 2 shows an example of a sequence of ultrasound pulses 54 having different frequencies. Two pulses are shown, but three or more pulses may be used. The bandwidth of the transducer may limit or determine the frequency separation and range of frequencies to be used. Assume N pulses are transmitted sequentially with time interval $T_1$ and an overhead time $T_o$ of the system. For example, pulses are transmitted at 3 MHz, 4 MHz, and 5 MHz. Each pair of sequential pulses are separated by a period 56 of no transmission associated with overhead time and any other period. Other transmissions may occur during the period 56. For example, ring down or system noise signals may result in some transmission, but at amplitudes less than the intended pulses.

The pulses are of any number of cycles. For example, three or more cycles may be used. A greater number of cycles may reduce the bandwidth of the pulses, allowing more complete pulse separation on receive. In one embodiment, each pulse is at least 4 cycles. Any envelope, type of pulse (e.g., unipolar, bipolar, or sinusoidal), or waveform may be used.

In act 38, ultrasound echoes are received in response to the transmit event. The echoes are responsive to the mutually orthogonal signals. The receive operation of act 38 starts at $(N-1)T_1$ and finishes at $T_o+(N-1)T_1+2Z/c$ for depth span Z and sound speed c. The PRF for transmit and receive is $1/(T_o+(N-1)T_1+2Z/c)$. Instead of receiving a sample at one location for a given transmit and receive event pair, a plurality of samples for the location are received, increasing the PRF. The signals are received at the different frequencies or including the code.

The echoes are received in a receive event. The receive event is a contiguous interval for receive echoes from the depth of interest. The event occurs after ceasing the transmit event. After the transducer completes generation of acoustic energy for transmission, the transducer is used for reception of the responsive echoes.

In act 40, tissue motion is detected. Motion responsive to a shear wave or other wave may be detected. The tissue motion is detected at different times. The different times correspond to the different signals in a given transmit event. The received echoes are separated into information responsive to different mutually orthogonal signals.

In one embodiment, the received signals are filtered as a function of frequency. Using memory and a programmable filter, the information is band pass filtered at different frequency bands to separate out the different signal responses. Alternatively, different paths with separate filtering are provided. Filtering alone is provided for separation. In another approach, the received echo signals are demodulated in one or more paths and filtered with low pass filters to generate base band information representing the signals at the desired frequency bands. For example, at the receiving in act 38, N in-phase and quad-phase demodulator pairs with corresponding center frequencies are provided. Each modulator is followed by a low pass filter. The PRF for the N pairs of IQ data is $1/T_1$, which may be much higher than the conventional pulse sequencing method may provide, $1/(T_o+2Z/c)$, for high Z value. N samples are provided for each transmit and receive event pair, where each of the samples represents the tissue response at a different time.

In another embodiment, the signals are transmitted as pulses having different codes. Matched filtering decodes the received signals responsive to coded transmission. The mutually orthogonal pulses are separated, in part providing samples at different times.

Tissue motion is detected from the signals at the different frequencies or separated by coding. Tissue motion is detected by estimating displacement relative to the reference tissue information. For example, the displacement of tissue along scan lines is determined. The displacement may be measured from tissue data, such as B-mode ultrasound data, but flow (e.g., velocity) information may be used. Correlation, cross-correlation, minimum sum of absolute differences or other similarity measure is used to determine the displacement between scans. For example, each IQ data pair is correlated to its corresponding reference to obtain the displacement. Data representing a plurality of spatial locations is correlated with the reference data. In one embodiment, the displacement estimation algorithm disclosed by Pinton, et al. in "Rapid Tracking of Small Displacements with Ultrasound," IEEE Trans. UFFC 53(6), pgs. 1103-1117, 2006, is used. The displacements are determined along one, two, or three dimensions.

The monitoring is performed for any number of scan lines. For example, four receive beams are formed in response to each transmission. After transmitting the acoustic force to generate the shear wave, B-mode transmissions are performed repetitively along a single scan line and receptions along four adjacent scan lines. Some of the ultrasound data, such as at the beginning or end of the repetitions, may not be responsive to the shear or other wave. In other embodiments, only a single receive beam or other numbers of receive beams are formed in response to each transmission. Each repetition monitors a same region or locations for determining tissue response for those locations.

As the shear wave propagates through the scan lines, the B-mode intensity may vary. For the monitored scan lines, a sequence of data is provided representing a time profile of tissue motion resulting from the shear or other wave. For example, data from a plurality of spatial locations (e.g., along the scan lines) is correlated as a function of time. Any elasticity detection may be used. For each depth or spatial location, a correlation over a plurality of depths or spatial locations (e.g., kernel of 64 depths with the center depth being the point for which the profile is calculated) is performed. The spatial offset with the highest or sufficient correlation at a given time indicates the amount of displacement. For each location, the displacement as a function of time is determined. Two or three-dimensional displacement in space may be used. One-dimensional displacement along a direction different than the scan lines or beams may be used.

The detection of tissue motion occurs while or after the echoes are received. In one embodiment, the received information is stored and may be used for later detection. In other embodiments, the received information is used for detection as the data is received.

In act 42, the transmission and reception acts 36, 38 with or without the detection act 40 are repeated. The repetition is for different transmit and receive events. The transmission of the N signals is repeated to provide N samples at different times. Any number of M repetitions may be used, such as repeating about 50-100 times. The repetitions occur as frequently as possible while the tissue recovers from the stress, but without interfering with reception. The tissue temporal displacement profile is obtained by repeatedly transmitting to and receiving signals from the same target area in a similar way as the Doppler method does. To generate the temporal displacement profile, a series (M) of N pulses are transmitted and received.

To monitor a larger region, additional receive beams are formed in response to the monitoring transmit beam. Alternatively, another shear wave is generated and the transmit beams and receive beams are provided at a different distance from the shear wave generation point. In a 6 mm×10 mm monitoring region example, 36 receive scan lines may be provided. At four receive beams per transmit beam, the process is repeated for different lateral spacing nine times. For each receive beam location, a time profile of motion information is provided, represented by the ultrasound data. Transmissions along different scan lines to monitor a same shear wave are avoided during formation of the temporal profile to provide higher temporal resolution, but interleaved or shifting scanning positions may be provided.

The samples may be acquired for one depth. Alternatively, the sampling may be arranged to provide one gate covering the entire axial extent of the region of interest. In another embodiment, samples are obtained at multiple depths for each receive beam. A separate time profile is provided for each axial depth as well as lateral location. Any number of depths may be used, such as about 200 for 5 mm or 400 for 10 mm.

Ultrasound data representing different locations in the region of interest is obtained. The ultrasound data is obtained in real-time with the scanning or obtained from a memory. Tissue motion for each location is determined as a function of time. For each location, the motion information represents the response at different times, providing a temporal profile. Other scanning, monitoring, or techniques may be used to obtain ultrasound data to estimate shear velocity.

Figure 3A:
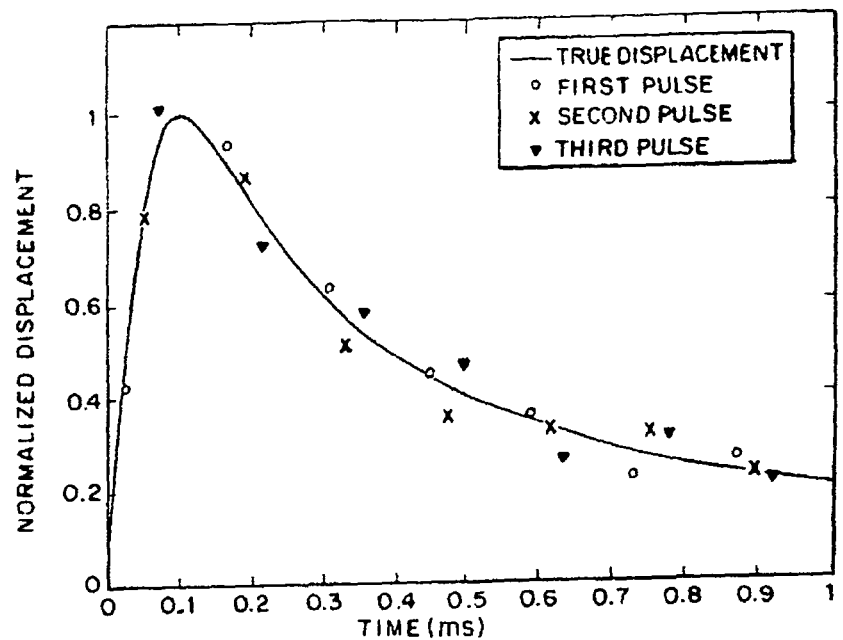
FIGS. 3a-d are an example graphical representation of a time profile of tissue motion information, such as displacements.
Figure 3B:
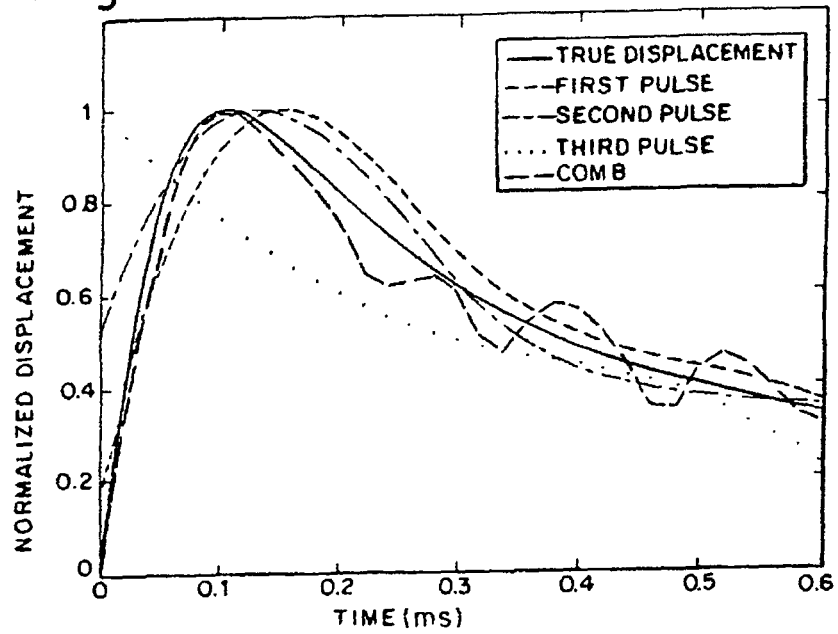

In act 44, the tissue response is determined as a function of the tissue motion. The tissue response is the temporal profile, a time of peak displacement, or other response. The tissue response is derived from the tissue motion. For example, the tissue motion is derived from the plurality of samples representing the displacement or strain at different times. FIG. 3 shows the displacement as a function of time. As shown in FIGS. 3a and 3b, triplets of displacement measurements are provided in close temporal proximity. These represent the transmission in a same event of three separable signals (e.g., 3, 4, and 5 MHz pulses). A plurality of repetitions of the transmit and receive acts 36, 38 provide samples over a longer period.

The temporal profile is determined as a function of tissue motion from at least two different transmit and receive events. The final displacement profile is reconstructed from all or a subset of the displacements. Displacement is estimated for IQ data sets derived from each center frequency, so MN displacement data points or N displacement profiles are generated. The data sampling rate for each profile is $1/(T_o+(N-1)T_1+2Z/c)$. A higher sampling rate profile is reconstructed from these N profiles.

The peak displacement may be identified by finding a maximum displacement. In an alternative embodiment, a curve is fit to the tissue motion samples. Any curve fitting may be used. For example, a regression is applied. Since the shear wave velocity is linear, a robust linear regression with automated outlier detection may indicate the shear wave velocity. The ultrasound data for all of the sample points in the region of interest is plotted for distance as a function of time or by time and distance. The linear regression is applied to the plot or data, providing a line fit to the data. In another example, a spline interpolation is used. After sorting the data of the N profiles according to their time stamp, cubic spline interpolation is used to reconstruct the final temporal displacement profile at a PRF of 1.0 MHz. In other embodiments, a Fourier transform is used. The curve is identified in the frequency domain after removing components at undesired frequencies. The inverse transform provides the time curve.

Figure 3C:
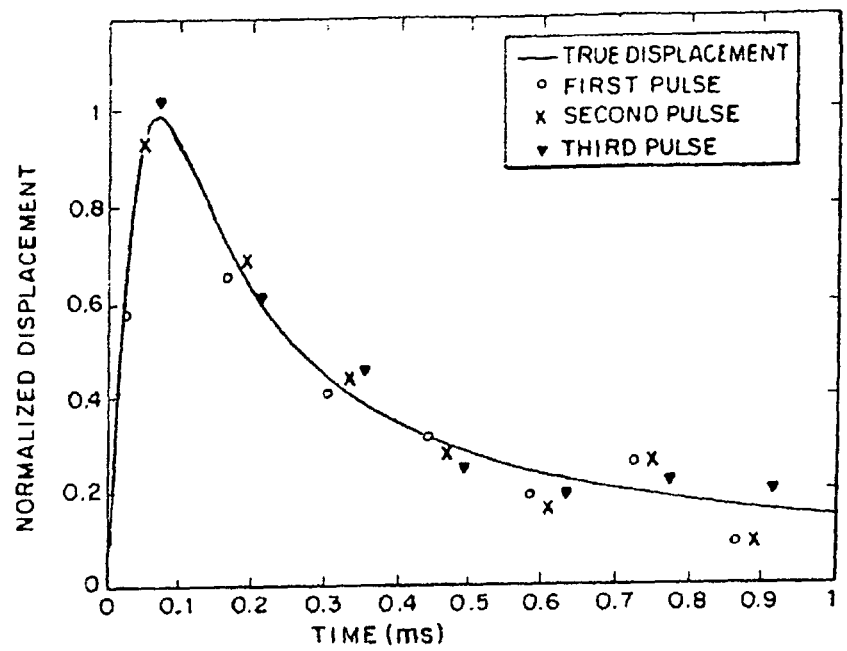
Figure 3D:
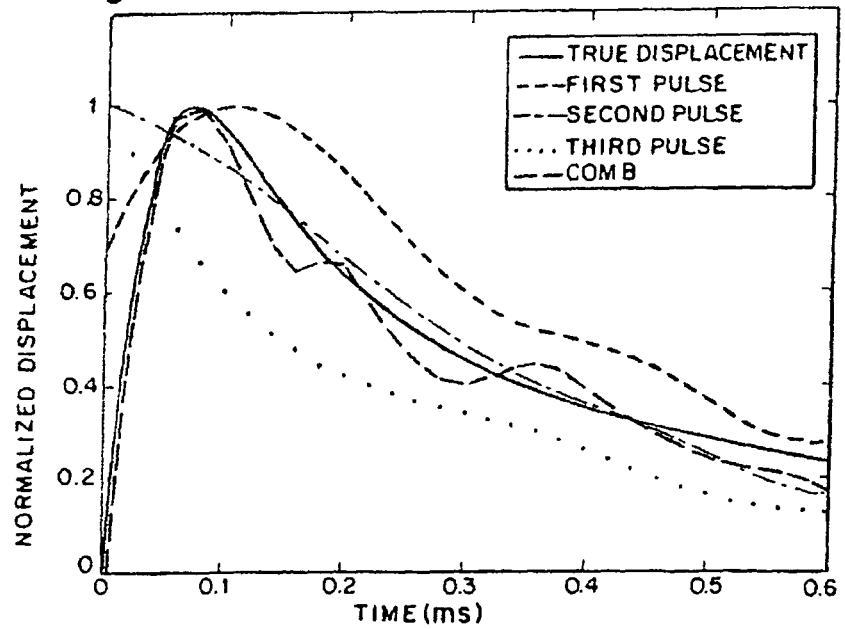

FIGS. 3a-d represent curves fit to the displacement samples. FIGS. 3a and b are for a modeled shear wave propagating at 7 m/s. FIGS. 3c and d are for a modeled shear wave propagating at 10 m/s. FIGS. 3b and d represent curves fit to the different separable signals (e.g., one curve for the 3 MHz signals, one for the 4 MHz signals, and one for the 5 MHz signals). FIGS. 3a and c show curves fit to all the samples.

The peak displacement may be calculated from the curve or temporal profile. The maximum displacement indicates the peak displacement. The peak displacement represents tissue displacement associated with the shear or other wave. The temporal profile for a given location indicates detection of the shear or other wave. A peak in the profile, with or without temporal low pass filtering, indicates the passing of the shear wave front.

In one example model, with M=7 and N=3, 2.0, 3.0, and 4.0 MHz pulses are transmitted with constant bandwidth of 1.0 MHz. To consider the potential noise from harmonic frequency, a low signal-to-noise ratio is assumed and is set to 20 dB. Scatters are displaced according to an analytic representation of a temporal displacement profile. The shear velocity is set to 7.0 m/s and 10.0 m/s. The results of this model are shown in FIGS. 3a-d. FIGS. 3a and c demonstrate the estimated displacements at sampling points along with the actual profiles. The black dashed-line, dot-dashed-line and dotted-line in FIGS. 3b and d show the cubic spline interpolation results of the estimated displacements for the first, second, and the third pulses. The reconstructed profile is shown with a solid line. The peak location in the reconstructed profile is closer to the true peak location compared with each individual profile. The distance between the peaks of the reconstructed profile and the true profile is measured and is used to indicate the accuracy of performance.

The tissue response, such as the peak, may be used as a result. Alternatively, further calculations are performed, such as in act 46. In act 46, a tissue mechanical property may be characterized as a function of the tissue response. The peak and its temporal location in the temporal displacement profile may be used to characterize tissue's mechanical property, such as strain, strain rate, elasticity, viscosity, impedance, or others.

Shear velocity is obtained by determining a time from generation of the shear wave until detection of the shear wave at a different location. The time and distance to the location determine the velocity. The distance is known from the scan line spacing (i.e., the transmit beam position for generating the shear wave and the receive beam position for detecting the shear wave). The time is known from the relative time between generation and detection of the shear wave. The peak indicates the shear wave.

As another example, a feature is extracted from the temporal profiles. Principle component decomposition may be used. A correlation between the different temporal profiles is performed. The lag associated with the different distances for the different temporal profiles provides the velocity. Alternatively, a wavelet analysis may be performed. A wavelet transform is applied to the temporal profiles to identify a peak or other characteristic corresponding to the shear wave. A velocity value is identified from the travel time of the peak to each spatial location.

In act 48, an image may be generated. The image is generated as a function of the tissue response. Shear information is displayed. Any shear information may be displayed. For example, the shear velocity is displayed. The shear velocity is for the region of interest. The velocity may be displayed on the image or without the image. A representation of shear velocity may be used instead of an actual number, such as mapping a color or otherwise modulating the pixels at the region of interest as a function of the shear velocity. For example, a high velocity is mapped to a brighter red than a lower velocity.

The shear velocity may be indicated relative to a range of shear velocities with or without other shear velocity information. For example, a bar, line, graph or other representation of a range of shear velocities is displayed. The range may be for tissue or may be specific to type of tissue. For example, the user inputs or a processor identifies the type of tissue for which velocity is measured. A range of normal and abnormal velocities for that type of tissue is output. The range does or does not indicate normal or abnormal velocities. The estimated shear velocity is shown on the range, such as an arrow or other indicator of the estimated shear velocity range. The relative position may be more intuitive to a user.

The displacement may be used to generate the image. For example, the image pixels are modulated by the peak displacement. As another example, the image pixels are modulated by the time to the peak displacement. Such an image may indicate regions or locations associated with different (e.g., slower or faster) response to the shear wave. Any tissue response imaging may be used, such as strain, strain rate, elasticity, shear wave or other now known or later developed imaging.

FIG. 4 shows one embodiment of a system 10 for detection of tissue response with high pulse repetition frequency. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for manual or assisted selection of display maps, tissue properties to be determined, region of interest selection, selection of transmit sequences, coding selection, or other control. The system 10 is a medical diagnostic ultrasound imaging system. In alternative embodiments, the system 10 is a personal computer, workstation, PACS station, or other arrangement at a same location or distributed over a network for real-time or post acquisition imaging, so may not include the beamformers 12, 16 and transducer 14.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. The transmit beamformer 12 generates and causes transmission of a cascade of pulses with mutually orthogonal codes, such as a sequence of pulses with different frequencies or other coding.

Upon transmission of acoustic waves from the transducer 14 in response to the generated waves, one or more beams are formed. A sequence of transmit beams are generated to scan a two or three-dimensional region. Sector, Vector®, linear, or other scan formats may be used. The same region is scanned multiple times. For flow or Doppler imaging and for strain imaging, a sequence of scans are used. In Doppler imaging and shear velocity estimation, the sequence may include multiple beams along a same scan line before scanning an adjacent scan line. For strain imaging, scan or frame interleaving may be used (i.e., scan the entire region before scanning again). In alternative embodiments, the transmit beamformer 12 generates a plane wave or diverging wave for more rapid scanning.

The transmit beams are formed at different energy or amplitude levels. Amplifiers for each channel and/or aperture size control the amplitude of the transmitted beam. Transmit beams to generate a shear wave and/or for strain imaging may have greater amplitudes than for imaging or monitoring for the shear wave.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer. The elements connect with channels of the transmit and receive beamformers 12, 16.

The transmit beamformer 12 and receive beamformer 16 connect with the same elements of the transducer 14 through a transmit/receive switch or multiplexer. The elements are shared for both transmit and receive events. One or more elements may not be shared, such as where the transmit and receive apertures are different (only overlap or use entirely different elements).

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to a transmission. In alternative embodiments, the receive beamformer 16 is a processor for generating samples using Fourier or other transforms.

The receive beamformer 16 may include a filter, such as a filter for isolating information at desired frequency bands. A band pass filter, or demodulator and band or low pass filter may be used. In other embodiments, the filter includes a modulator for applying matched filtering to filter with matching codes such that separate signals are generated in response to a coded transmission. For rapid detection, parallel paths may be provided for receive beamforming separately for different frequencies or separated signals. Alternatively, a processor operating pursuant to software performs the filtering, beamforming, or combinations thereof.

The receive beamformer 16 outputs beam summed data representing spatial locations at a given time. Data for a single location, locations along a line, locations for an area, or locations for a volume are output. Dynamic focusing may be provided. The data may be for different purposes. For example, different scans are performed for B-mode or tissue data than for shear wave velocity estimation. Data received for B-mode or other imaging may be used for estimation of shear velocity.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, network, server, group of processors, data path, combinations thereof or other now known or later developed device for detecting and processing information for display from beamformed ultrasound samples. In one embodiment, the processor 18 includes one or more detectors and a separate processor. The processor 18 performs any combination of one or more of the acts shown in FIG. 1.

The processor 18 is operable to detect tissue motion as a function of the separate signals from a same transmit event. The processor 18 detects the tissue motion at different times from the separate signals and reference information. Using repetition of the cascaded pulses or coded waveforms and corresponding filtering, data for a region over a range of times is detected. Using the data, tissue motion over a range of times is detected. The tissue motion responsive to a shear wave is calculated. The peak displacement, displacement profile, shear wave velocity or other information is estimated. For example, the processor 18 estimates shear velocity by detecting a time for the shear wave to travel a distance. The time selected for a given location corresponds to the peak in the displacement profile. Multiple estimates may be provided and/or data from different locations used for one estimate. Linear regression, correlation, principle component extraction, wavelet transforms, cubic spline interpolation, or other estimation techniques may be used.

The processor 18 generates display data, such as graphic overlays and images. The display data is in any format, such as values before mapping, gray scale or color-mapped values, red-green-blue (RGB) values, scan format data, display or Cartesian coordinate format data, or other data. The processor 18 outputs data appropriate for the display device 20.

The processor 18 operates pursuant to instructions stored in the memory 22 or another memory. The processor 18 is programmed for detection with high pulse repetition frequency of tissue response. The memory 22 is a computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display device 20 is a CRT, LCD, projector, plasma, printer, or other display for displaying shear velocity, graphics, user interface, validation indication, two-dimensional images, or three-dimensional representations. The display device 20 displays ultrasound images, the shear velocity, and/or other information. For example, the display 20 outputs tissue response information. The displayed information is in a report or screen presentation and is a function of the tissue motion. An image representing the tissue response to the shear wave may be output.

The display device 20 is operable to output a velocity range associated with a type of tissue and indicate the estimated shear velocity within the range. Since the velocity is a function of the peak displacement, the more rapid PRF provided by transmitting mutually orthogonal pulses in a same transmit event may result in more accurate velocity determination. The display device 20 receives the graphics information for this output from the processor 18. The display device 20 generates a visual representation of the graphic, such as the bar or other range scale. An indication of the estimated shear velocity relative to the range is also generated, such as generating an arrow, color, bar, text, or other graphic adjacent to, overlaid on, combined with, or associated with the range.

The display device 20 outputs an image of a region of the patient, such as a two-dimensional elasticity, Doppler tissue, or B-mode image. The image includes a location indicator for the shear velocity. The location relative to the imaged tissue for which shear velocity is calculated is shown. The shear velocity is provided on or adjacent the image of the region. Alternatively or additionally, shear velocity is determined for a plurality of locations and the image pixels are modulated as a function of the shear velocity for spatially representing shear velocity.

In the modeling, the average mean and standard deviation from the velocity range 6 to 10 m/s are 1.4+/8.8 µs in the proposed method, and 24.6+/−3.9 µs in conventional method (single sample per location in response to each transmit). Due to the extra signals transmitted, even if in a rapid sequence, imaging at shallow depths may be limited. The shallow dead zone starts from the transmit/receive surface to the depth of $c*(T_o+(N-1)T_1)$, and can be reduced by lowering the number of transmit pulses N and shorting $T_1$.

In other embodiments, the transmission of mutually orthogonal signals to increase PRF is used for analysis of myocardium and/or vessel wall motion. Rather than transmission of acoustic radiation force, the displacement of tissue caused by cyclical motion of the heart is determined. Differences in displacement may indicate differences in tissue characteristic. By increasing the effective PRF, more accurate tissue characteristics may be estimated.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for determining tissue mechanical property, the method comprising:

transmitting, in a first transmit event and with a transducer, a plurality of overlapping ultrasound signals at different frequencies to tissue responding to stress, the signals of the first transmit event being mutually orthogonal along a common scan line at a single spatial location;

receiving, in a first receive event and with the transducer, ultrasound echoes responsive to the mutually orthogonal signals, wherein the first receive event occurs after completion of the first transmit event;

detecting, using a computer, tissue motion at a plurality of times corresponding to the plurality of overlapping signals, respectively, as a function of the received echoes from the first receive event, wherein the function comprises distinguishing the ultrasound echoes responsive to different signals of the plurality of overlapping signals transmitted along the common scan line for the single spatial location and at the plurality of times being during performance of a single event pair of the first transmit event and the first receive event;

determining, using the computer, tissue response as a function of the tissue motion;

wherein the tissue response is a temporal profile of the tissue or a time of peak displacement of the tissue; and determining, using the computer, a tissue mechanical property as a function of the tissue response.

2. The method of claim 1 further comprising:

transmitting, in a second transmit event prior to the first transmit event, the plurality of signals to the tissue prior to application of the stress;

detecting reference tissue information in response to the transmitting of the second transmit event; and transmitting acoustic radiation force, the tissue responding to stress comprising the tissue responding to the acoustic radiation force;

wherein detecting comprises estimating displacement relative to the reference tissue information.

3. The method of claim 1 wherein the detecting tissue motion comprises detecting motion responsive to a shear wave.

4. The method of claim 1 wherein the detecting comprises filtering as a function of frequency.

5. The method of claim 1 wherein the transmitting in the first transmit event comprises transmitting the signals as a coded waveform, wherein the first receive event occurs after completion of the first transmit event, and wherein detecting comprises filtering matched to the coded waveform.

6. The method of claim 1 further comprising:

imaging as a function of the tissue response.

7. The method of claim 1 further comprising:

repeating the transmitting, receiving and detecting for at least second transmit and receive events;

wherein the determining the tissue response comprises determining as a function of tissue motion from at least the first and second transmit and receive events.

* * * * *